(12) United States Patent
Apple et al.

(10) Patent No.: US 7,056,274 B2
(45) Date of Patent: Jun. 6, 2006

(54) CATHETER WITH CONCENTRIC BALLOONS FOR RADIOGAS DELIVERY AND BOOSTER RADIOSOURCES FOR USE THEREWITH

(76) Inventors: Marc G. Apple, 1606 Sycamore Hills Dr., Ft. Wayne, IN (US) 46804; William D. Voorhees, III, 1020 W. 850 North, West Lafayette, IN (US) 47906

( * ) Notice: Subject to any disclaimer, the term of this patent is extended or adjusted under 35 U.S.C. 154(b) by 162 days.

(21) Appl. No.: 10/195,829

(22) Filed: Jul. 12, 2002

(65) Prior Publication Data
US 2003/0032851 A1    Feb. 13, 2003

Related U.S. Application Data

(60) Provisional application No. 60/305,315, filed on Jul. 13, 2001.

(51) Int. Cl.
*A61M 29/00* (2006.01)
*A61M 5/32* (2006.01)
*A61M 25/00* (2006.01)

(52) U.S. Cl. ..................... 600/3; 604/101.02
(58) Field of Classification Search ............. 600/1–8; 604/258, 264, 101.01, 101.02, 101.04
See application file for complete search history.

(56) References Cited

U.S. PATENT DOCUMENTS

| | | | |
|---|---|---|---|
| 5,059,166 A | 10/1991 | Fishell et al. | |
| 5,141,487 A | 8/1992 | Liprie | |
| 5,213,561 A | 5/1993 | Weinstein et al. | |
| 5,302,168 A | 4/1994 | Hess | |
| 5,616,114 A * | 4/1997 | Thornton et al. | ............... 600/3 |
| 5,662,580 A * | 9/1997 | Bradshaw et al. | ............. 600/3 |

(Continued)

FOREIGN PATENT DOCUMENTS

EP    0266957 A2    10/1987

(Continued)

*Primary Examiner*—Samuel G. Gilbert
(74) *Attorney, Agent, or Firm*—Taylor & Aust, P.C.

(57) ABSTRACT

A catheter assembly for use in radiation therapy of a patient by insertion into a vessel, passageway or cavity to deliver radioactive material to a treatment site within the patient. The distal end of the catheter assembly (10) includes a noncompliant inner balloon (18) therearound that is inflatable with a non-radioactive fluid (such as $CO_2$ or saline or contrast medium), and an outer balloon (16) therearound that is inflated with radioactive fluid (such as radiogas like xenon-133 ) and is noncompliant to conform the vessel wall to the balloon's shape at the treatment site for optimal distribution of dose. The inner balloon allows reduction in volume of the amount of radioactive fluid necessary to achieve a desired dose. The inner and outer balloons (112, 108) may be affixed to inner and outer catheters (104,102), respectively. Further, a booster radioactive source, preferably removable from the catheter, may also be used to supplement the dose from the outer balloon, such as a radioactive line source (a wire or a seed train (118,234)) within the central catheter lumen (116,230) at the distal end, or a plurality of seeds (320) within flexible cylinders (318) spaced circumferentially around the inner balloon (308) but within the outer balloon (310), or a sleeve (402) around the inner balloon (406) that may be impregnated with iodine-125. A method of providing radiation therapy is disclosed.

10 Claims, 6 Drawing Sheets

U.S. PATENT DOCUMENTS

| | | | |
|---|---|---|---|
| 5,913,813 A * | 6/1999 | Williams et al. ................ | 600/3 |
| 5,916,143 A | 6/1999 | Apple et al. | |
| 5,924,973 A * | 7/1999 | Weinberger ..................... | 600/3 |
| 6,117,064 A | 9/2000 | Apple et al. | |
| 6,123,712 A * | 9/2000 | Di Caprio et al. .......... | 606/108 |
| 6,152,869 A * | 11/2000 | Park et al. ..................... | 600/3 |
| 6,162,165 A | 12/2000 | Apple et al. | |
| 6,251,059 B1 | 6/2001 | Apple et al. | |
| 6,458,069 B1 * | 10/2002 | Tam et al. ..................... | 600/3 |
| 6,605,030 B1 * | 8/2003 | Weinberger ..................... | 600/3 |
| 2003/0078538 A1 * | 4/2003 | Neale et al. ............. | 604/98.01 |

FOREIGN PATENT DOCUMENTS

| | | |
|---|---|---|
| WO | WO 99/12609 | 3/1999 |
| WO | WO 00/04953 | 2/2000 |

\* cited by examiner

CATHETER WITH CONCENTRIC BALLOONS FOR RADIOGAS DELIVERY AND BOOSTER RADIOSOURCES FOR USE THEREWITH

The present application is a continuation-in-part of co-pending provisional application Ser. No. 60/305,315, filed Jul. 13, 2001.

FIELD OF THE INVENTION

The present invention relates to the field of medical devices and more particularly to catheters for delivery of radioactive material to a treatment site in a patient.

BACKGROUND OF THE INVENTION

Angioplasty is an established procedure for reducing the effect of atherosclerotic plaque on and intraluminal narrowing of the arterial walls within the vascular system of the patient. The effect is reduced by use of a catheter that is inserted into the site of the diseased-occluded vessel. A balloon portion of the catheter is then inflated to a predetermined pressure range and size, to radially compress the plaque occlusion, thereby increasing the internal diameter of the previously restricted artery. The balloon is then collapsed and the catheter is removed.

After the angioplasty procedure has been performed, as many as one-third to one-half of the patients soon develop restenosis. Restenosis can occur after angioplasty or other recannulation procedures, with or without stenting, wherein the migration and proliferation of benign cells cause a restenotic lesion to form, resulting in the further blockage of the intravascular structure.

Radiation is administered to patients for a variety of reasons, such as to treat restenosis, malignant or benign tumors, or the like. Examples of such treatments are disclosed in U.S. Pat. Nos. 5,059,166; 5,213,561; and 5,302,168.

A catheter system is known from U.S. Pat. No. 5,916,143 to Apple et al, and also from WO 99/12609, wherein an inert radioactive fluid such as a gas, like xenon-133, is delivered endovascularly to a treatment site in a patient, for treatment of restenosis after angioplasty, and for malignancies. When the catheter's balloon arrangement is inflated, it may include a plurality of discrete chambers for transporting the radio-gas, and the catheter also includes a plurality of discrete chambers enabling substantial blood flow through the artery during treatment with the prescribed radiation.

Known xenon-133 single-balloon systems provide excellent shallow depth dose rates to 0.5 mm in easily handleable quantities in short treatment times. However, higher activity quantities or greater treatment times are required to obtain deeper depth dose profiles and could then create too high a surface dose without balloon wall thickening to screen out lower energy electrons.

Another form of radiation treatment utilizes seed or wire systems, such as those having iodine-125 or utilizing iridium-192. One such brachytherapy source wire is disclosed in U.S. Pat. No. 5,141,487 in which a source wire comprises iridium-192/platinum wire within a platinum sheath. Another is described in WO 00/04953, in which a brachytherapy device is a needle that is adapted to implant into a patient, seeds comprising an iridium-192/platinum alloy encased within plastic.

Known iodine-125 sources are not made to activity levels that are high enough for, or that are practically designed for, short term high dose rate brachytherapy for vessels or non-solid organs. They are inherently poorly centered and non-conformal in a thin catheter. At millimeter tissue distances, it does not provide higher needed shallow dose rates although providing better deeper dose rates for complete target minimal dose coverage.

It is desired to provide a radioactive source treatment system that is particularly suitable for endovascular use in larger arteries, for use with large diameter lumen catheters, and also that is useful for treatment of larger hollow cavity organ sites.

It is also desired to maintain limited treatment times, limited radioactivity quantities and controllable, variable-depth doses and dose rates for different sites.

SUMMARY OF THE INVENTION

The foregoing problems are solved and a technical advance is achieved in an illustrative minimally invasive medical device for providing a radiation treatment in a body passageway such as a vessel in the vascular system. The catheter assembly includes a balloon arrangement having a noncompliant or minimally compliant outer balloon for containing the radioactive fluid such as an inert radioactive gas, and an inner displacement balloon that is separately filled with fluid ("fluidically distinct"). Use of an inner balloon of substantial diameter upon inflation, reduces the volume in which the radioactive gas resides within a target vessel or passageway, thereby reducing the amount of radioactive gas required for treatment. Preferably, the inner balloon is also noncompliant, and as a result there will be a substantially constant spacing between the inflated inner balloon and the outer balloon's outer wall. Upon inflation of both inner and outer balloons, the outer balloon will define a cylinder of radioactive fluid of limited thickness pressing against the patient's vessel wall at the target site, conforming well to the vessel wall.

The inflation lumen for the outer balloon is small to minimize the amount of gas in the catheter and maximize the amount of gas in the balloon, while the inner balloon inflation lumen is much larger for the delivery of nonradioactive fluid such as contrast fluid. Optionally, the inner balloon can have an outer treatment or material that changes the properties of the radioactive particles which contact the surface. Preferably the fluid for the inner balloon is contrast media. Inflation of the inner balloon forces more of the radiogas to be closer to the tissue; therefore, increasing the pressure of the radiogas is equivalent to increasing its concentration.

In another aspect of the invention, a catheter assembly is adapted for use with additional radioactive sources such as seeds or guidewire, and is particularly adapted for removable radioactive sources for multiple treatment procedures of those sources. Such a catheter assembly may combine both the radiofluid-filled outer balloon and the removable non-fluid radioactive sources, such as seeds, that boost the effective dose above that provided with the radiofluid-filled outer balloon alone. The booster radioactive sources may be in the form of elongate seed trains placed around and along the length of the inner balloon. The booster radioactive sources may also be in the form of a sleeve containing radioactive seeds or material between the inner and outer balloons, for surrounding the inner balloon and that expands and collapses with inflation and deflation of the inner balloon.

In an additional aspect of the present invention, the inner balloon may be affixed to an inner catheter of small diameter, while the outer balloon containing radiofluid would be affixed to an outer catheter of larger diameter, with the catheters being preassembled to each other prior to insertion into a patient over a guide wire, or the catheters being sequentially inserted into a patient over a guide wire, preferably with the use of insertion depth markings on both at their proximal ends.

BRIEF DESCRIPTION OF THE DRAWINGS

Embodiments of the present invention will now be described by way of example with reference to the accompanying drawings, in which.

DETAILED DESCRIPTION

FIGS. 1 to 7 disclose a concentric balloon arrangement of the present invention. FIGS. 8 to 13 illustrate booster radioactive sources of the present invention, for use with the concentric balloon arrangement of FIGS. 1 to 7, but could be used separately from the concentric balloon arrangement of the present invention. FIG. 14 is useful with all the embodiments of FIGS. 1 to 13.

As used herein, the term "fluid" includes any gas, liquid, or gel-type substance that generally conforms to the shape of the container within which it is held, and is fluent. While the catheter apparatus of the present invention is used in conjunction with a radioactive carrier fluid, it is preferred that the fluid is a gas, and for reasons hereinafter set forth, an inert gas, such as preferably xenon, or an isotope of xenon. However, the present invention is not limited to xenon gas or an isotope thereof, and the preferred fluid includes all gases and isotopes thereof, radioactive gases or radiogases (inert and/or non-inert) or gases capable of fluorescence, phosphorescence, or luminescence (electron stimulation). Examples of gases include, but are not limited to, xenon, krypton, neon, radon and their isotopes. A radiogas can be dissolved in a liquid or solution (sterile) such as sterile water or saline and be used as a liquid radiofluid. Liquids include all isotopes of liquids and solutions. An isotope can be radioactive or non-radioactive. Radioactive includes nuclear (nucleus) decay of an atom. A radionuclide is any radioactive atom. Fluorescence, phosphorescence or luminescence is associated with electron instability and subsequent emission of radiant energy. Liquids also include all gasses dissolved in liquids or solutions. Examples of liquids include, but are not limited to, liquid phosphorus, rhenium, yttrium, technetium, iodine, gallium, chromium, strontium, thallium, samarium, ytterbium, palladium, and all isotopes thereof, and all compounding and binding solutions thereof. All gels utilizing the aforementioned gases or liquids (solutions) are also contemplated. Additional radionuclides can include osmium, vanadium, ruthenium, bismuth, or other transitional heavy metals and their isotopes for liquid and/or gel-type compounding. All inert dual photon/electron emitting radionuclides are further contemplated as well as all inert single particle radio-emitting nuclides and all non-inert radionuclides thereof. Still further contemplated are all inert or non-inert radiofluids which use electron stimulation to produce by-product fluorescent, phosphorescent or luminescent radiant energy for patient treatment. The use of by-product radiant energy emissions including fluorescent, phosphorescent or luminescent emissions can be utilized for therapeutic treatment. Implementation of radionuclide and by-product radiant energy emissions can be applied by the use of the catheter apparatus in the following combinations;

(a) gases and/or fluids or single fluids alone either as a gas—gas or gasliquid, and/or either inert or non-inert, and/or radioactive or non-radioactive such that the photon or electron emissions of one radiofluid can induce electron shift, scatter, or a quantum level change in the electron shell of the same or other combined "fluid" atoms thereby causing production of relatively low energy photon/electron (possibly in a cascaded amplification) emissions into the targeted tissue as a controlled/calculated dose;

(b) radiofluid(s) as described in (a), except that induction of listed radiant energy is provided via electrical source stimulation from an electrode, cathode, wire or other transmission source such that controlled electrical currents and/or electrical potential delivered through the catheter to the radiofluid or non-radiofluid of the balloon catheter which causes expected electron excitation and/or quantum level fluctuations with by-product fluorescence, phosphorescence and/or luminescence for the aforementioned therapeutic treatments; and (c) phosphorus and/or other known fluorescent metals or alloys are implanted in the balloon material and/or catheter structure so that the combinations described in (a) and (b); radioemission, by-product decay energy and/or direct electrical stimulation can cause effect on the implanted/layered materials so as to create fluorescent, phosphorescent or luminescent energy delivery as these materials stabilize their electron structure after such stimulation.

The radiation dose rate of a balloon material is a function of or is dependent upon the thickness of the balloon material, the density of the balloon material, and/or the volume of the balloon. In addition, the volume is, in turn, dependent upon the length of the radiation source and, in particular, the longitudinal length of the balloon along with the diameter and radius of the balloon. The axial length of the balloon is important with respect to the radiation source in that accumulative dosimetry effects (scatter, coincidence, photo electric) are achieved with the radioactive fluid disposed along the length of the catheter. The radiation dose rate is also effected by the surface area of the inflatable balloon in response to the radioactive fluid.

Radiation source activity is a function of the radioactive fluid or preferably of the radioactive gas that is used with the radiation treatment. As described hereinafter, radioactive xenon-133 gas is preferred in that it is an inert gas that provides synchronous gamma and beta radiation emission with a half life of approximately five days. Concentrations of xenon-133 gas can typically range from 10 mCi to 150 mCi per cc or more of gas volume at the time of calibration. Radioactive xenon-133 gas, and less commonly used xenon-127 gas and krypton 85, as well as, technetium compounds, have been widely used for several years and proven relatively safe within medically accepted radiation levels for nuclear diagnostic studies involving the lung and the measurement of blood and fluid flow rates through vessels to specific organs. When used as an unsealed free-gas form, the inert, noble gas properties essentially enable the molecules to rapidly dissipate throughout the body of the patient or through a room, without any prolonged organ accumulation or interaction within specific dose ranges. Any xenon that enters the bloodstream is quickly released to the air within the lungs as the blood passes therethrough, and is then exhaled.

Xenon is a very stable element which can be pressurized, stored, and made to high millicurie activity per cubic centimeter (cc) with very reasonable cost and availability.

Xenon-133 provides both a beta particle (101 kev avg.; 364 kev max.), and at least two usable photons (32 kev 48 percent; 81 kev 37 percent).

The beta particles offer excellent initial dose rate delivery when directly adjacent to the tissue within the first millimeter. The particle does not penetrate much beyond the first millimeter of tissue, thereby not contributing to any significant distal normal tissue exposure.

The gamma photon energies and their decay fractions provide complementary dose deposition for the first millimeter, and primary dose delivery for an additional several millimeters of arterial wall and adjacent tissue. The high percent of attenuated, and lower energy photons beyond this point provide for ease of personnel protection with routine lead jackets, or by placing a cover over the external surface of the treated region. Furthermore, the sensitivity of a small field gamma camera provides simple image monitoring and dose evaluation simultaneously.

Xenon-133 is commercially available within a week in concentration ranges from 10 mCi to 200 or 300 mCi or more per cc of gas volume. Also, the cost is currently estimated to be less than a few hundred dollars a dose of 150 mCi. A single dose order can be used to treat several patients per day for a full week, as the physical half-life is 5.2 days, although this may be impractical since some percentage loss of gas is expected to occur during transfer. Also, no special equipment, storage, or delivery devices are necessary, except for routine facilities available in most nuclear medicine or radiation oncology departments.

In vivo and in vitro facilities with standard exhaust hoods or negative pressure rooms provide adequate protection for this sealed use of xenon gas. A metered dose can safely and readily be transported to nearly any treatment site by one person, and administered by one person without special radiation protection needs, such as is necessary with higher energy photon sources for conventional brachytherapy. The most expensive addition to a standard treatment room is a simple negative pressure ventilation system, as a backup safety mechanism.

Radiation exposure time is prescribed by the attending physician, commonly with a speciality in radiation oncology, nuclear medicine or nuclear oncology. Exposure times range from less than a minute upwards to ten minutes, depending on the activity of the radiation source. Particular concentrations of the radiation source are normally provided with commercially available radiation sources. These concentrations are used by the physician to determine radiation exposure time. The radiation dose rate is a function of the properties of delivery devices, which in turn is a function of balloon material thickness, density and volume. An external or internal brachytherapy medical radiation delivery device can be experimentally dose calibrated and verified by a radiation physician specialist, medical physicist, or certified radio/nuclear laboratory, or with approved device-specific computer software for patient treatment. With such a calibrated radiation dose rate, the physician can calculate and prescribe the required radiation source concentrations and exposure times for treatment of the patient. The calibration of the delivery device typically includes positioning the delivery device in a phantom and positioning radiation detectors/sensors at a prescribed distance away from the delivery device in the phantom. A series of measurements are used to graph the radiation from a series of radioactive fluid concentrations applied thereto. Such calibration is necessary and demanded by various regulatory agencies so that the radiation treatment provided to a patient is within specified limits of the prescribed total radiation dose.

Figure 1:
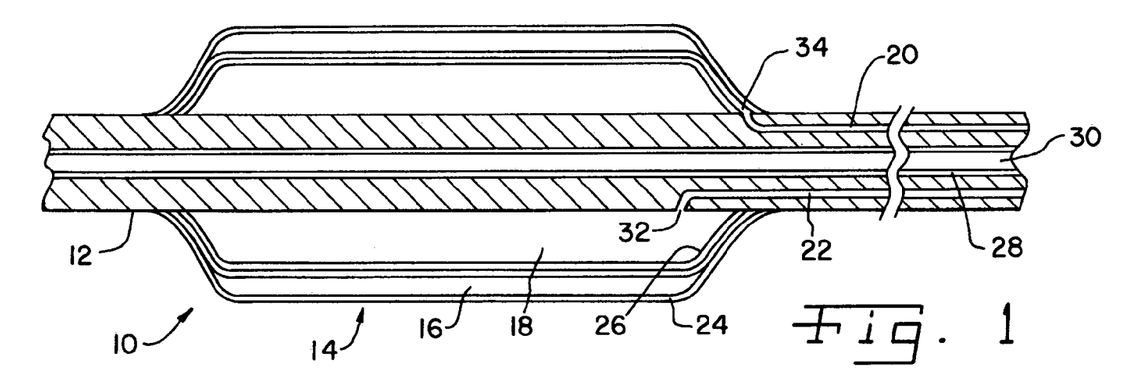
FIG. 1 is a part sectioned view of a first embodiment of the present invention, showing the distal end of an endovascular concentric balloon arrangement assembly having inner and outer balloons.

The embodiment shown in FIG. 1 is a balloon catheter assembly 10 with a distal end 12 having a balloon section 14 wherein an outer balloon 16 surrounds an inner balloon 18, each with a discrete, separate inflation lumen 20 or 22. The inner balloon 18 upon inflation insures a stable outer balloon configuration and displacement. The diameters of the outer and inner balloons are preferably in a prefixed ratio, that provides assured outer balloon volume, depth dose profile and conformal tissue interaction. Outer balloon 16 may be made of material such as polyethylene, so that its outer wall 24 is noncompliant or minimally compliant to conform the local vessel topography to the balloon's shape for optimum distribution of dose; such materials may be of various densities or thicknesses, and may include metal or metal alloy filler materials. Outer balloon 16 will be inflated with the radiofluid, such as xenon-133 and should be labeled "Radiofluid (or Radiogas) Only".

The inner balloon 18 may be made of polyethylene material and preferably is noncompliant, being expandable to a controlled outer diameter. Its outer wall 26 may be thicker, and/or metallized, and/or inelastic compared to that of the outer balloon. Inner balloon 18 would be inflated by a nonradioactive fluid, such as $CO_2$, saline or a contrast medium, and would be labeled "Non-Radioliquid Only"; preferably the inner balloon is of a material that is impermeable and impervious to radiogas to prevent contamination of the fluid used with the inner balloon. It is preferred that the distal ends of the outer and inner balloons converge as they are joined to the catheter shaft, and the proximal ends as well, so that the inflation of both balloons results in a cylinder of radiogas. It is believed that shielding of the catheter shaft is unnecessary; its small lumen, and its placement within a guiding catheter, will result in minimal activity of the radiofluid at the outermost surface of the catheter and no effect on nearby surrounding tissue.

Shielding materials may include high density material of at least one of barium, tungsten, lead, tantalum, titanium, bismuth, gold, platinum, palladium, rhodium, or any other similar suitable material. A coating on the outer wall of the inner balloon may include a gas/fluid impermeable layer of nontoxic, unreactive carbon-chain/polymer based substances; which may also be integrated with metal alloy components to create scatter and/or brehmsstrahlung byproduct radiation effects.

Additionally, coatings and/or integrated ferromagnetic alloys or alloys of equivalent metallic properties may be utilized to extract the clinical benefit of secondary hyperthermia effects, including empirically self-regulating by "alloy properties", such that the radiation emissions and the physics of their interaction with the ferromagnetic (or equivalent) elements creates local increased heating of the tissue. The maximal temperature range of the catheter wall and the tissue would be a predictable value. (i.e., 45° C.±10%) such that known radiobiologic advantages with combined radiotherapy and hyperthermia could be exploited for treatment benefits, such as better efficacy, shorter treatment times or doses, and so forth.

The catheter assembly 10 would have three distinct lumens: a guide wire lumen 28 for guide wire 30, an inflation lumen 22 of large diameter for the inner balloon 18, and a small diameter lumen 20 for inflating the outer balloon 16 with radiogas, with the inflation port 32 for the inner balloon being distal to the inflation port 34 for the outer balloon.

Catheter assembly 10 also includes proximal controls (not shown) and connectors of the type disclosed in U.S. Pat. No. 5,916,143, and would include separate controls for the radiofluid and the nonradioliquid for the outer and inner balloons, respectively.

The outer balloon may have specific sites where a thicker and/or denser wall would be desired to exploit predominant penetration of only highest energy Beta particles and/or photons, thereby providing a totally different depth dose profile. Optionally, the catheter may have a magnetizing section at the balloon section, for subjecting the radiogas to a magnetic flux for electron acceleration of gas in outer balloon; such a catheter assembly is disclosed in U.S. patent application Ser. No. 09/748,327 filed Dec. 26, 2000. Also, the inner balloon wall 26 may have outpouching folds, or either concentric and/or longitudinal ribbed pocketing at intervals, would decrease the net volume and increase the internal pressure of the gas/fluid injected within the space between the inner and outer balloons, to allow greater compression and decreased volume of the outer balloon.

Figure 2:
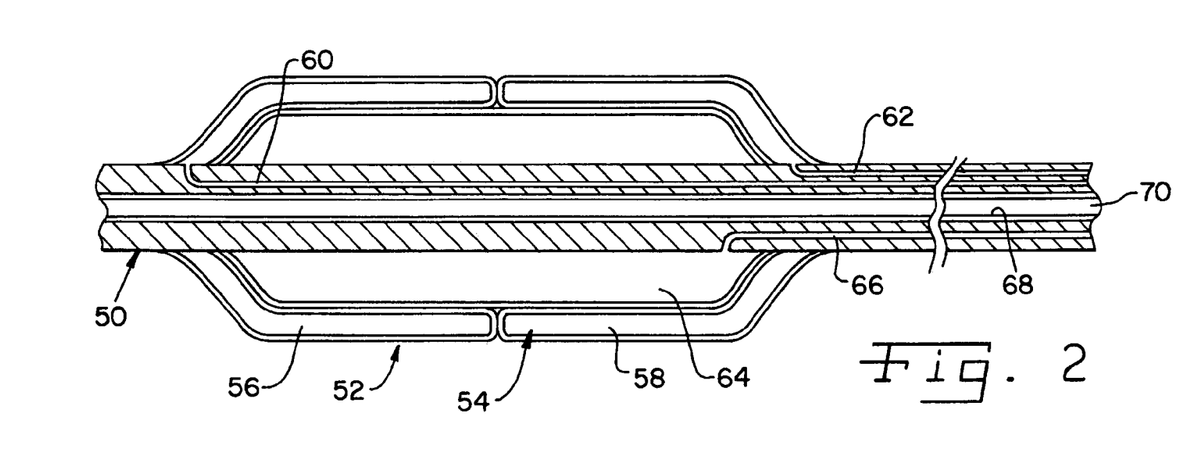
FIGS. 2 and 3 are a part sectioned elevation view of the distal end of a second embodiment of concentric balloon arrangement assembly having a split outer balloon, and a cross-section view of the catheter shaft.
Figure 3:
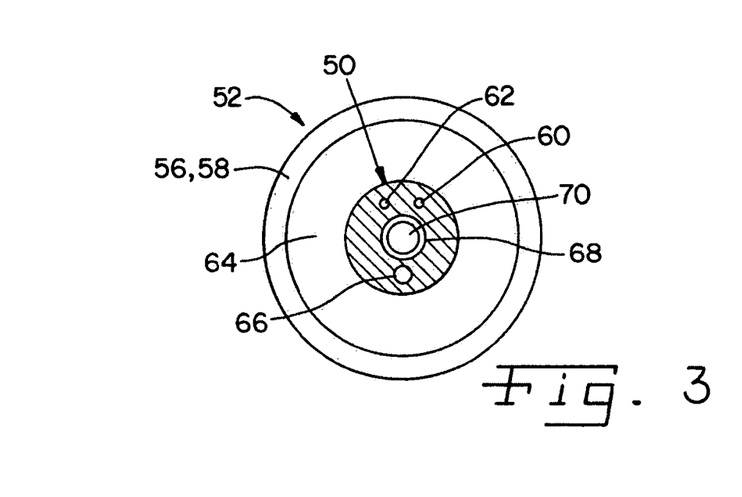

In the embodiment of FIGS. 2 and 3, the balloon section 52 of catheter assembly 50 includes an outer balloon 54 that is segmented into distal and proximal halves or segments 56, 58 that provide conformal shape and pressure balanced distribution. Each of the distal and proximal halves or segments 56, 58 have separate inflation lumens 60, 62, while the inner balloon 64 may be singular and have a single inflation lumen 66, to simplify construction. Catheter assembly 50 would also have a guide wire lumen 68 for a guide wire 70. Preferably, a single lumen would be utilized to inflate both segments 56,58 of the outer balloon.

Figure 4:
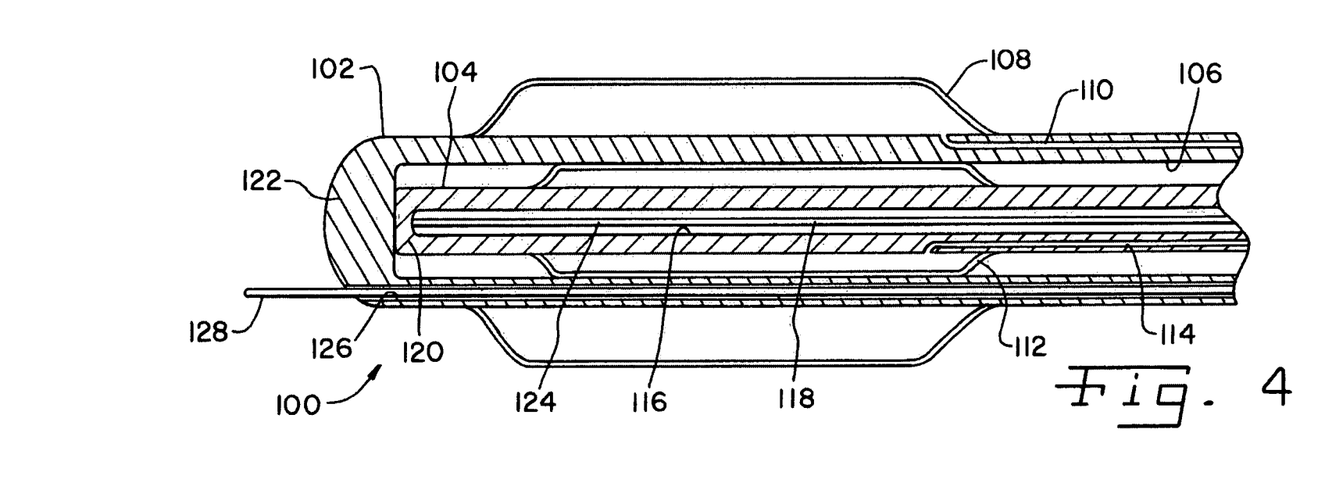
FIGS. 4 and 5 are a part sectioned elevation view of the distal end of a third embodiment of concentric balloon arrangement assembly utilizing a booster radioactive line source, and a cross-section view of the catheter shaft.
Figure 5:
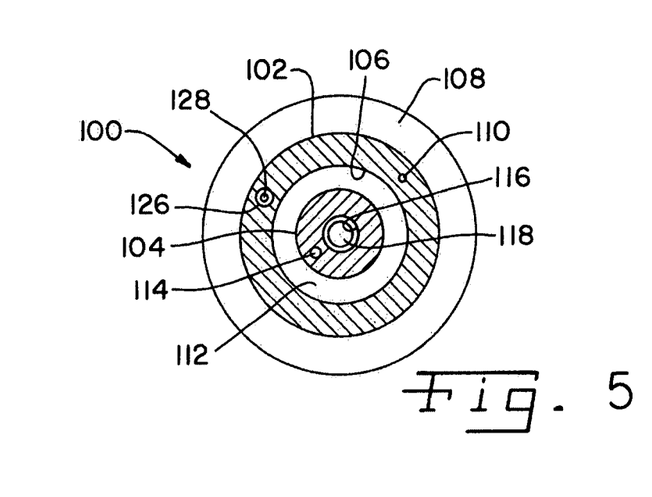

In FIGS. 4 and 5 is disclosed a catheter assembly 100 that is adapted for larger vessel applications such as, for example, esophageal, biliary, and pulmonary. Catheter assembly 100 includes a large diameter outer catheter 102 and a small diameter inner catheter 104. Outer catheter 102 has a large diameter central lumen 106 and has affixed thereto a radiogas-filled outer balloon 108 and an inflation lumen 110 therefor. Small diameter inner catheter 104 has an inner balloon 112 affixed thereto, and an inflation lumen 114 therefor. Upon assembly, the outer balloon 108 is concentrically disposed about inner balloon 112, and inner balloon is self-centering within central lumen 106 of outer catheter 102, and is supportive of the wall of large catheter 102 underlying outer balloon 108. A booster radiosource is utilized in this embodiment, to attain depth dose acceleration. Inner catheter 104 has a centered inner lumen 116 for a radioactive line source 118 such as a radioseed or radiowire source. Line source lumen 116 has a closed distal end 120, and central lumen 106 of large catheter 102 also has a closed distal end 122, so that the inner catheter is positively stopped during insertion into the outer catheter upon abutment of its closed distal end 120 with closed distal end 122, and line source 118 is positively stopped by closed distal end 120 of line source lumen 116 resulting in the radioactive distal end portion 124 of line source 118 being axially positioned centered with respect to outer balloon 108 at the desired treatment site; line source 118 is also radially centered within outer balloon 108 by self-centering inner balloon 112.

Preferably the channel or lumen 126 for the guide wire 128 extends along and within the wall of the large catheter 106, to eliminate affecting the centering of the radioactive line source lumen 116. Optionally, though, a small diameter tube could be affixed along and to the inside surface of the catheter wall. The outer balloon 108 is preferably thin-walled and conformal for radiogas under low pressure. The inner balloon 112 would be filled with a nonradioactive fluid such as $CO_2$ or a radio-opaque (contrast) liquid and would be inelastic with thickened walls and be presized to match the larger catheter's diameter.

In a further embodiment of catheter assembly 200 shown in FIGS. 6 and 7, again for larger vessel application, a booster radioactive source is again inserted through an inner catheter. A larger outer catheter 202 has affixed thereto the compliant outer balloon 204 and defines an inflation lumen 206 therefor along and within its wall. A smaller diameter inner catheter 208 is affixed within the large diameter bore 210 of outer catheter 202. Inner balloon 212 is affixed to the inner catheter to underlie the outer balloon 204 and has an inflation lumen 214 extending thereto along and within the inner catheter wall. In this embodiment, the wall of the outer catheter underlying the outer balloon includes a large annular recess 216 therearound (dividing the outer catheter into a tip section and a proximal section), such that upon inflation the inner balloon 212 protrudes through the recess and outwardly beyond the outer surface 218 of the outer catheter and thus protruding "into", and thus reducing, the standard volume of the outer balloon. Inner balloon 212, as before, is made of noncompliant material to expand to a preselected maximum diameter, and thus defines a support of known diameter for the outer balloon. Upon inflation of the balloon, the inner balloon presses radially outwardly against the conformal inner wall 220 of the outer balloon 204, and the radioactive fluid presses the conformal outer wall 222 of the outer balloon 204 outwardly to engage the wall of the large vessel, passageway or cavity, with a ratio of inflated inner balloon diameter to-inflated outer balloon diameter preferably being fixed to be about 0.80 to 0.90.

Figure 6:
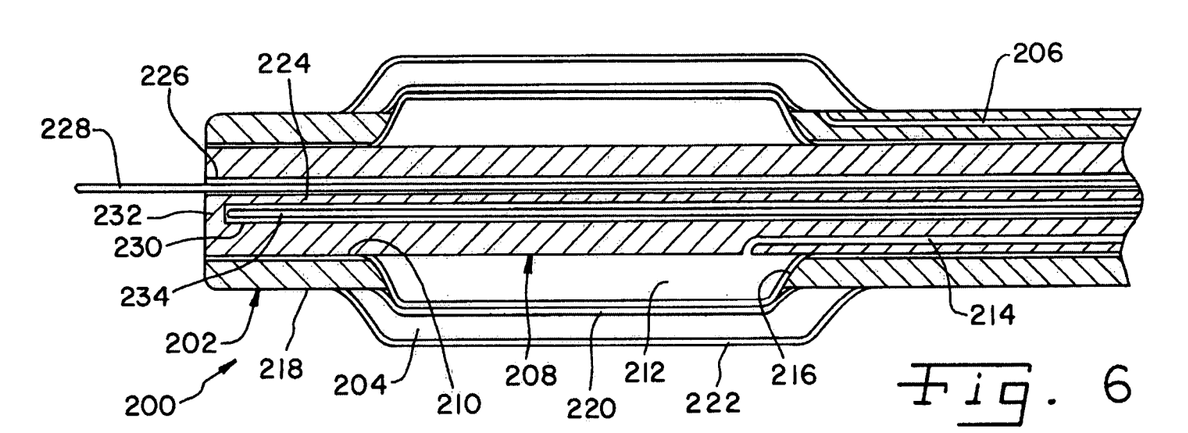
FIGS. 6 and 7 are a part sectioned elevation view of the distal end of a fourth embodiment of concentric balloon arrangement assembly and a cross-section view of the catheter shaft, utilizing a booster radioactive line source similar to that of FIGS. 4 and 5.
Figure 7:
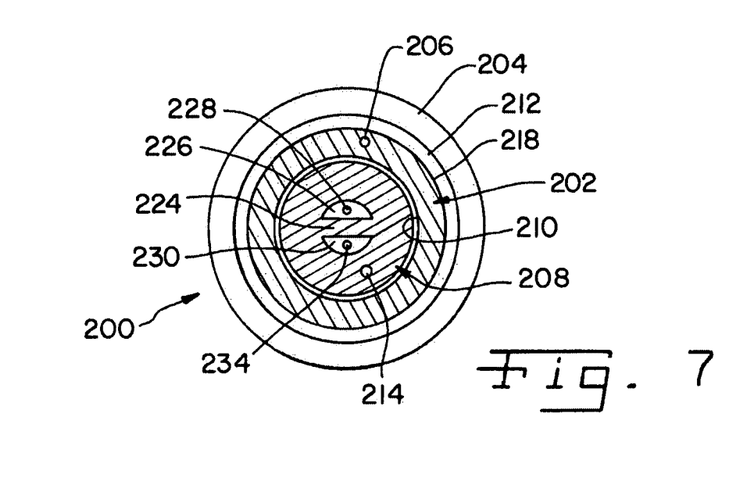

In catheter assembly 200, the inner catheter 208 defines centrally therethrough a channel that is bifurcated by a septum or inner wall 224, into a guide wire lumen 226 extending completely therethrough for delivery of the catheter assembly 200 along guide wire 228, and a line source lumen 230 that has a closed distal end 232 that serves as an insertion limit for appropriate placement of the radioactive line source at the treatment site. The radioactive line source 234 would be inserted along line source lumen 230 after placement of the catheter assembly distal end 236 at the treatment site, but before inflation of the inner and outer balloons 204,212 as a booster radiosource for depth dose acceleration.

For large vascular or for nonvascular applications such as esophageal, bladder, biliary tree, the device may be inserted under direct visualization, or palpation, or via the larger bore internal diameter of an endoscope, and so the device need not have a guide wire nor a guide wire lumen.

Figure 8:
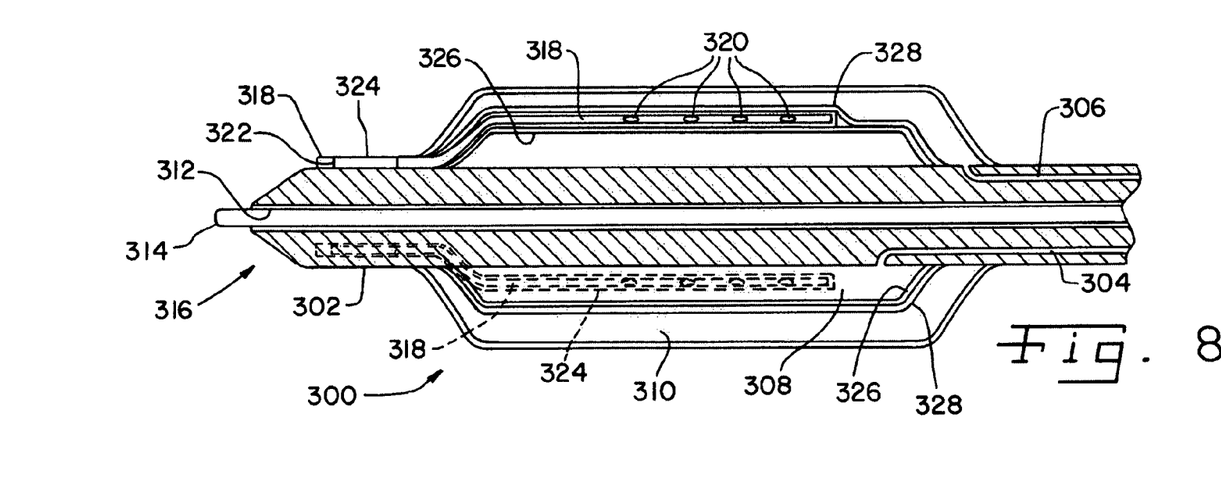
FIGS. 8 and 9 are partially sectioned elevation and cross-sectional views respectively, of another embodiment of the invention using seed trains, with FIG. 9 taken through the balloon section after inflation.
Figure 9:
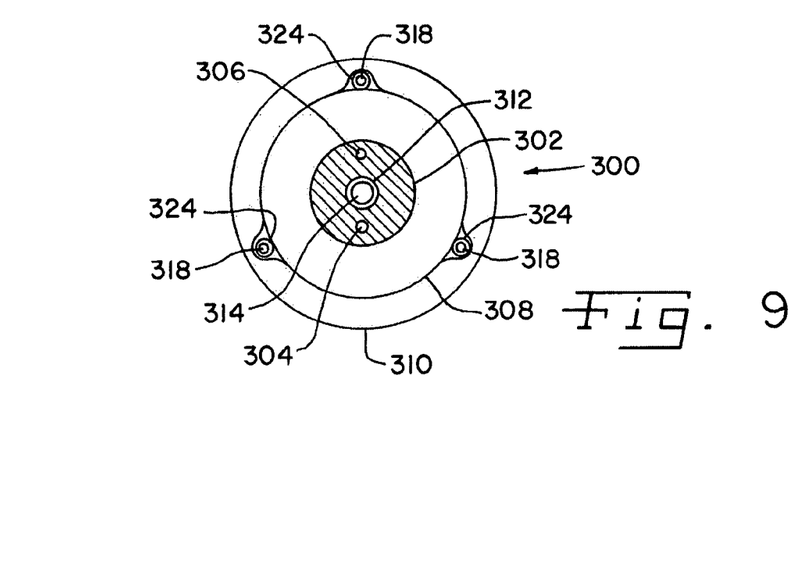
Figure 10:
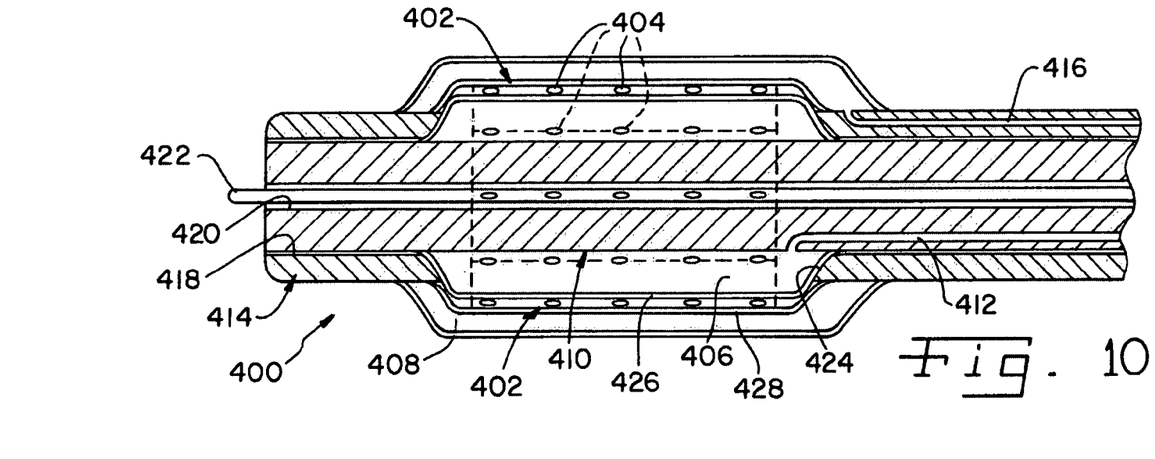
FIGS. 10 to 13 illustrate another embodiment of catheter assembly of the present invention, with a sleeve of radioactive sources shown in isometric view in FIG. 11, with FIGS. 12 and 13 being cross-sectional views before and after inflation of the inner balloon.

The embodiment of FIGS. 8 and 9 is also directed to a catheter system 300 particularly suitable for applications involving large vessels or non-solid organs, and utilizes the concept of a booster radioactive line source with partial perfusion allowance. The catheter 302 has only three lumens, with two inflation lumens 304,306 for the respective inner and outer balloons 308,310, and a third lumen 312 for the guidewire 314 extending to and through the distal end portion 316 of the catheter. At the distal end portion 316, a plurality of sealed and closed flexible elongate hollow plastic cylinders 318 are disposed along the distal end portion 316 prior to treatment. Elongate cylinders 318 are sealed at each end, and each contains several iodine-125 seeds 320 separated by spacers, together defining seed trains. The flexible elongate cylinders when in position within distal end portion 316 of catheter 302, in turn position the iodine-125seeds 320 axially centered along the balloon portion, with the seeds radially positioned between the walls of the inner and outer balloons 308,310. The cylinders 318 and their seeds 320 are disposed at spacings that are angularly equal about the circumference of the inner balloon 308. For example, three such line source seed trains would be at 120° about the circumference of the inner balloon, as shown in FIG. 9; four such seed trains would be at 90° about the circumference of the inner balloon. Each of the cylinders 318 would be inserted into the catheter system 300 through distinct loading ports 322 at the catheter's distal end and into distinct seed train lumens 324 (all outwardly of the catheter outer surface) along the outer surface of outside wall 326 of the inner balloon 308 and radially inwardly of the inner wall 328 of the outer balloon 310. Optionally, the loading ports 322 of the seed train lumens 324 could permit removal of the line source cylinders 318 from the catheter assembly following a treatment procedure, for use in another such catheter assembly after standard resterilization; such radioactive line sources could be reused for about two months or so.

Figures 11, 12:
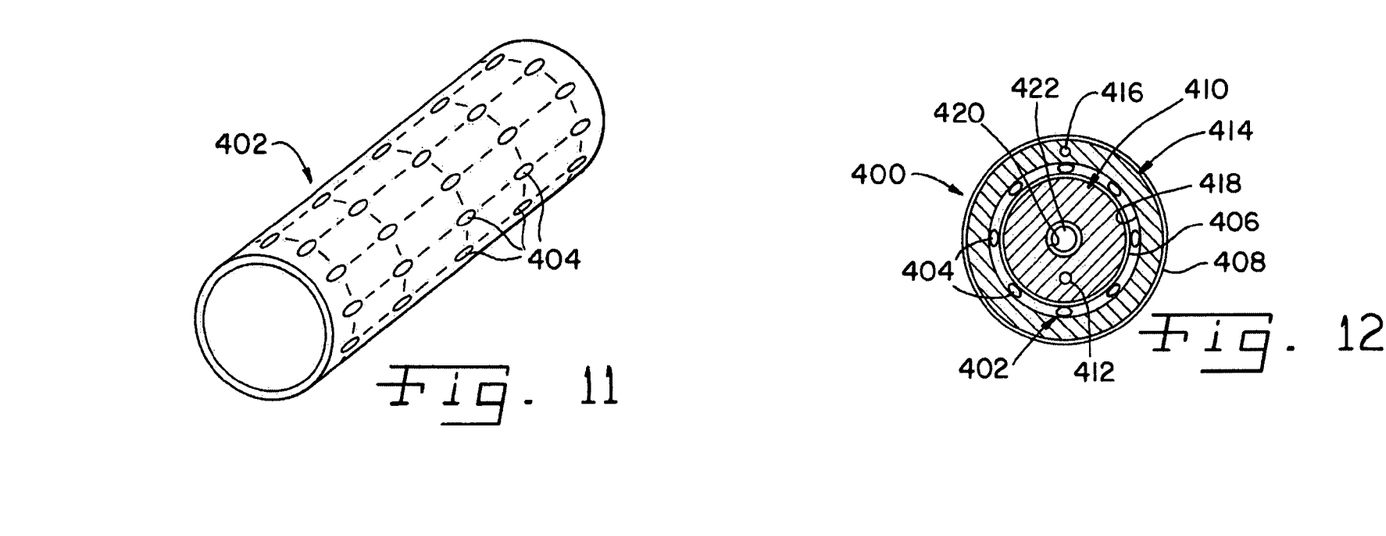
Figure 13:
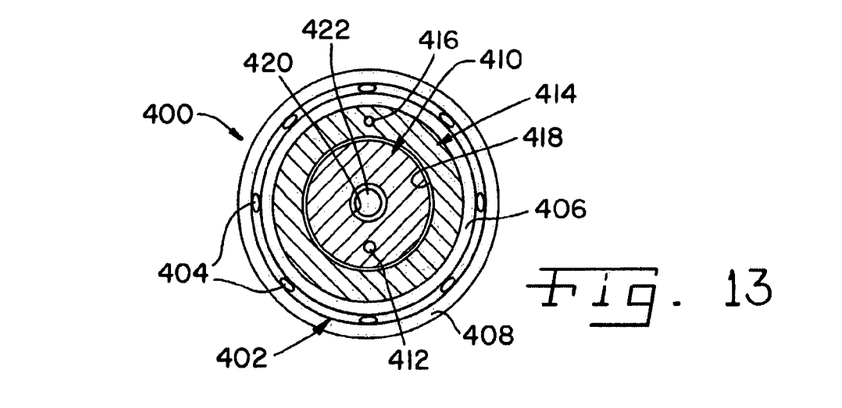
Figure 14:
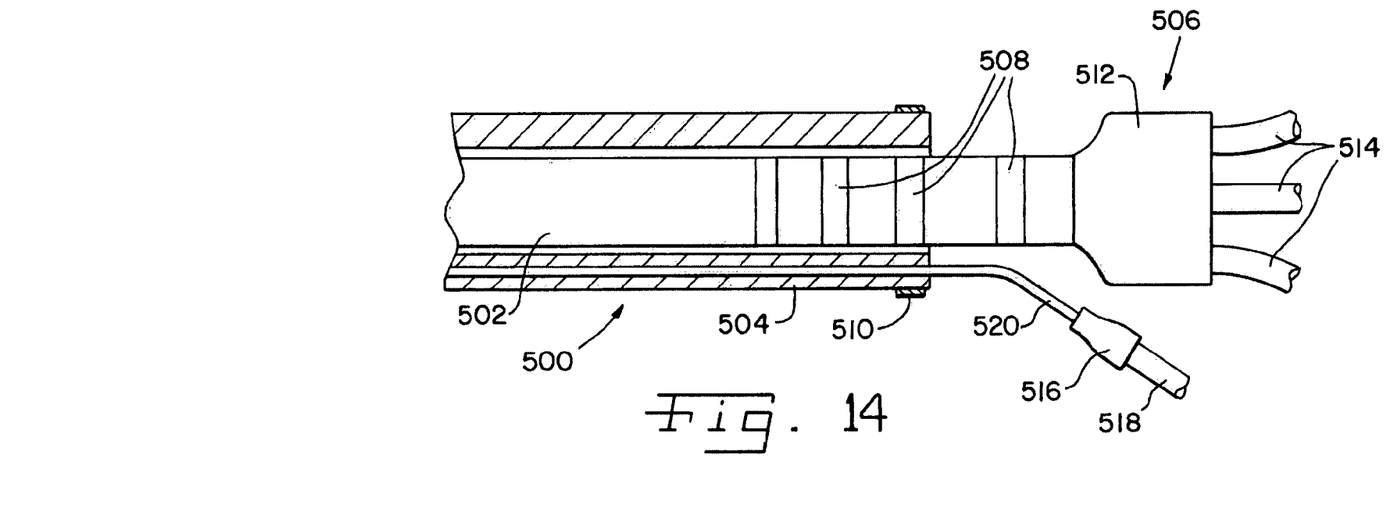
FIG. 14 is a partial isometric view of the proximal end of a catheter assembly of the present invention, with insertion depth markings and showing inner and outer catheters.

In FIGS. 10 to 13, a catheter assembly 400 has a seed sleeve 402 containing a plurality of radioactive sources such as line sources or such as seeds 404 therealong and therearound, such as iodine-125, or seed sleeve 402 could be impregnated with iodine-125. Iodine-125 has a half life of about sixty days and its use is cost-effective. Seed sleeve 402 would be useful best as a booster radioactive source supplementing the xenon-133-filled outer balloon of the present invention, and it is disposed prior to treatment around the inner balloon 406 but within the outer balloon 408, and is collapsible and expandable with inflation of the inner balloon 406, to boost the radioactive dosage, and seed sleeve 402 would be recollapsible with inner balloon deflation. FIGS. 12 and 13 illustrate the catheter assembly in cross-section, with the balloons uninflated and the seed sleeve collapsed in FIG. 12, and the balloons and seed sleeve fully expanded in FIG. 13. Again, inner balloon 406 would be inelastic and relatively high pressure-filled with $CO_2$ or fluid such as saline or contrast fluid. Preferably, inner balloon 406 could be affixed to an inner catheter 410 defining inner balloon inflation lumen 412, while outer balloon 408 could be affixed to a second or outer catheter 414 having outer balloon inflation lumen 416. Outer catheter 414 would have a central lumen 418 larger in diameter than the outer diameter of inner catheter 410, with the diameter of the outer catheter lumen 418 also being sufficiently large to permit collapsed inner balloon 408 with seed sleeve 402 therearound to be disposed therewithin for ease of assembly. Inner catheter 410 would have a central lumen 420 for guide wire 422.

As with the concentric balloon embodiment of FIGS. 6 and 7, the outer catheter could be provided with an annular recess 424 for the seed sleeve and the inner balloon's outer wall 426 to protrude outwardly therethrough upon inflation, thus pressing against the inner wall 428 of the outer balloon, while the inner balloon would be inelastic and attain a fixed preselected outer diameter upon inflation. Catheter assembly 400 would be inserted as a unit into the patient. Optionally, the outer balloon may actually have a shared wall with the inner balloon, whereby the shared wall serves as both the inner wall of the outer balloon and the outer wall of the inner balloon.

Seed sleeve 402 could be made of superelastic material such as nitinol. The plurality of seed sources 404 could be disposed on seed sleeve 402 in rows and columns forming a grid, as seen in FIG. 11, with the grid containing about forty or so seed sources, for example. Seed sleeve 402 could also be of ferromagnetic alloy or alloys of platinum, niobium, gold, tantalum, titanium, Beta titanium, austenite, martensite or conichrome. Radioelements could include radionucleides of palladium, iodine, gold iridium, yttrium, strontium, ytterbium, xenon, krypton, samarium, rhenium, cobalt, cesium, and so on. Impregnation could be by ionization/laser processes, chemical-electro binding, or be of preformed tubing with direct radio/nuclear activation. The use of seed sleeve 402 would enable delivery and set-up that is simplified and predictable and conformal to areas served by deeper depth dose rates with maintained shallow high dose rates plus short treatment times. Seed sleeve 402 could be removed from the assembly and subjected to standard resterilization for subsequent reuse.

The catheter systems of the present invention shown in FIGS. 4 to 13 would allow for synchronized, concomitant and conformal boost brachytherapy such that readily available and safe quantities of both radiosources are optimized to provide desired shallow and deeper optional dose rates with short treatment times. Outer balloon deflation/reinflation options can be applied to provide an initially higher shallow dose delivery, then a continued deep dose delivery while the outer balloon is deflated, with perfusion allowance and conformal maintenance of the solid radiosource. Treatment total time in vessels could then still be kept to six minutes or less with partial perfusion, or to less than fifteen minutes in cavity organs like the esophagus, the bladder, and so forth.

Referring now to FIG. 14, catheter assembly 500 includes a smaller inner balloon catheter assembly 502 with an inner balloon (not shown) at its distal end within a larger diameter balloon catheter assembly 504 having an outer balloon (not shown) at its distal end, each having ports for inflation devices (not shown) and inflation lumens for their respective balloons. Catheter assembly 500 is provided with insertion depth markers or indicia adjacent to the proximal end 506, to assist in accurate insertion into the patient for the balloons and booster radioactive sources, if used, to assuredly reach the treatment site. A first set of markers 508 is placed on the inner catheter assembly 502 such as being spaced single centimeters apart, and a second marker 510 or set of markers 510 is placed on the outer catheter assembly 504. One or more markers 510 on outer catheter assembly 504 are to correspond with a selected respective marker or markers 508 on inner catheter assembly 502 so that when matched indicate ideal booster radiation delivery. An inappropriate match level mark relative to the larger catheter could indicate inadequate placement depth and/or wrongly selected 1° catheter. Markings may also be color coded to match appropriately selected catheter size, diameter of balloon or arterial location. A connector 512 is secured to the proximal end of the inner catheter and has a plurality of sealed ports 514; a connector 516 with a sealed port 518 is affixed to the proximal end of the outer balloon inflation lumen 520 extending from the outer catheter assembly 504.

Optionally, a pre-fixed or insertable/removable smaller internal displacement balloon allows preferably for use of $CO_2$ gas as the inflation medium which provides much less attenuation of energy from the indwelling/inserted radioactive line source prior to the radiation reaching the tissue surface, while the inflated inner balloon centers the line source. A liquid such as saline could also be substituted in the inner balloon. Then as an option, xenon-133 gas or its radioactive equivalent would then go into the outer balloon, thus boosting the line source radiation while maintaining centering.

Balloon-in-balloon displacement of the present invention may alone provide a good xenon-133 concentration and outward abutment with the target tissue, with proper inner balloon/outer balloon ratios of diameters (0.8 to 0.9) and wall thicknesses. The inner balloon should be noncompliant and should have a fixed outer diameter upon inflation. The outer balloon should also be noncompliant and may have variable thicknesses depending on site of treatment and desired depth dose and related screening out of lower energy Beta particles.

Basic Method:

1) A guide wire is inserted into the patient's vessel until its distal tip just passes the target site.

2) Either (a) if a single-unit assembly is being utilized, the catheter with its balloons uninflated, is inserted into the patient over the guide wire until its distal end reaches the target site; the catheter could be a catheter having a large diameter; or (b) if a two-catheter system is being utilized, the primary catheter with a large diameter and its outer balloon uninflated, is first placed over the guide wire and its distal end delivered to the treatment site, and then a smaller secondary catheter with a non-radiofluid balloon is placed into a special lumen port of the primary catheter and delivered to the target site within the uninflated outer balloon.

3) The inner balloon is inflated with a preselected volume of $CO_2$ or a contrast liquid (if needed).

4) Xenon-133 gas is injected into the outer balloon port.

5) After passage of the desired treatment time given, with or without perfusion as desired, the xenon-133 gas is withdrawn as much as possible, the nonradioactive fluid in inner balloon is withdrawn as much as possible.

6) Finally, the whole catheter system is removed from the patient and the balloon catheter(s) is/are discarded.

If booster radioactive sources are utilized with the concentric balloons of the present invention, step 2 is modified depending upon which type of booster source adapter is being used. For example, with regard to FIGS. 4 and 5, the smaller secondary catheter includes the line source therewithin so that the line source is carried to the treatment site by the smaller catheter.

With regard to FIGS. 6 and 7, step 2 is modified by insertion of the line source into the line source lumen of the inner catheter after the inner catheter has been fully inserted into position.

With regard to the seed train embodiment of FIGS. 8 and 9, step 2 is modified to accommodate the seed trains, which are installed into the distal end of the single catheter into respective lumens prior to insertion of the catheter into the patient as a complete assembly.

And with the use of the seed sleeve of FIGS. 10 to 13, the seed sleeve is assembled around the uninflated inner balloon, and together the inner catheter (with the sleeve around the inner balloon) is inserted as a subassembly into the larger outer catheter, preferably prior to insertion of the larger catheter into the patient; however, the larger outer catheter may be inserted into the patient first, after which the inner catheter subassembly could be then inserted.

In any of the booster radioactive source arrangements of FIGS. 4 to 13, the radioactive line source may be removed from the catheters for sterilization and reuse.

While this invention has been described in detail with particular reference to the preferred embodiments thereof, the principles and modes of operation of the present invention have been described in the foregoing specification. The invention is not to be construed as limited to the particular forms disclosed because these are regarded as illustrative rather than restrictive. Moreover, modifications, variations and changes may be made by those skilled in the art without departure from the spirit and scope of the invention as described by the following claims.

What is claimed is:

1. A catheter assembly providing a radiation treatment in a target tissue of a patient, comprising a balloon arrangement having an outer balloon for containing a radioactive fluid and a coaxially disposed inner displacement balloon that is separately fillable with nonradiofluid fluidically distinct from the radioactive fluid; the inner balloon of a substantial diameter relative to a diameter of the outer balloon whereby upon inflation, the volume in which the radioactive fluid resides within a vicinity of the target tissue is reduced, thereby reducing the amount of radioactive gas required for treatment, and lumens for communicating the radioactive fluid and the nonradioactive fluid from respective supplies to the outer balloon and the inner balloon respectively, whereby, upon inflation of both inner and outer balloons, the outer balloon defines a cylinder of radioactive fluid of limited thickness pressing against an interface of the target tissue at a target site, while conforming well to said interface, wherein an inflation lumen for the outer balloon has a first diameter and an inflation lumen for the inner balloon has a second diameter greater than the first diameter, whereby radioactive fluid in the catheter is reduced relative to the volume of radioactive fluid in the outer balloon while providing for delivery of the nonradioactive fluid to the inner balloon.

2. A catheter assembly providing a radiation treatment in a target tissue of a patient, comprising a balloon arrangement having an outer balloon for containing a radioactive fluid and a coaxially disposed inner displacement balloon that is separately fillable with nonradiofluid fluidically distinct from the radioactive fluid; the inner balloon of a substantial diameter relative to a diameter of the outer balloon whereby upon inflation, the volume in which the radioactive fluid resides within a vicinity of the target tissue is reduced, thereby reducing the amount of radioactive gas required for treatment, and lumens for communicating the radioactive fluid and the nonradioactive fluid from respective supplies to the outer balloon and the inner balloon respectively, whereby, upon inflation of both inner and outer balloons, the outer balloon defines a cylinder of radioactive fluid of limited thickness pressing against an interface of the target tissue at a target site, while conforming well to said interface, the inner balloon is fixed to a inner catheter of a first diameter and the outer balloon is fixed to an outer catheter of a second diameter greater than the first diameter for receiving the first catheter therein, wherein the lumens comprise a guide wire lumen for a guide wire to guide the insertion of the catheter assembly to the target site, a first inflation lumen of a first diameter communicating between a supply of the nonradioactive fluid and the inner balloon, and a second inflation lumen of a second diameter smaller than the first diameter and communicating between a supply of the radioactive fluid and the outer balloon.

3. A catheter assembly providing a radiation treatment in a target tissue of a patient, comprising a balloon arrangement having an outer balloon for containing a radioactive fluid comprising a first radiation source and a coaxially disposed inner displacement balloon that is separately fillable with nonradiofluid fluidically distinct from the radioactive fluid, the inner balloon of a substantial diameter relative to a diameter of the outer balloon whereby upon inflation, the volume in which the radioactive fluid resides within vicinity of the target tissue is reduced and controlled, thereby reducing the amount of radioactive gas required for treatment, and lumens for communicating the radioactive fluid and the nonradioactive fluid from respective supplies to the outer balloon and the inner balloon respectively, whereby, upon inflation of both inner and outer balloons, the outer balloon defines a cylinder of radioactive fluid of controlled and limited thickness pressing against an interface of the target tissue at a target site, said cylinder of a predetermined volume, while conforming well to said interface, the inner balloon is fixed to a inner catheter of a first diameter and the outer balloon is fixed to an outer catheter of a second diameter greater than the first diameter for receiving the first catheter therein, further including an additional radioactive source.

4. The catheter assembly of claim 3, wherein said additional radioactive source is a radioactive line source.

5. The catheter assembly of claim 3, wherein said additional radioactive source is a plurality of radioactive seeds.

6. The catheter assembly of claim 3, further including a separate lumen within said catheter assembly, said additional radioactive source is located in said separate lumen.

7. The catheter assembly of claim 6, wherein said separate lumen is located within said inner catheter.

8. A catheter assembly for providing a radiation treatment in a target tissue of a patient, comprising:
a balloon arrangement including at least one balloon, said balloon arrangement for containing a radioactive fluid comprising a first radioactive source, said balloon arrangement including an outer balloon for containing said radioactive fluid and a coaxially disposed inner displacement balloon that is separately fillable with a nonradiofluid fluidically distinct from the radioactive fluid, wherein said inner balloon is fixed to a inner catheter of a first diameter and said outer balloon is fixed to an outer catheter of a second diameter greater than said first diameter for receiving said first catheter therein; and
an additional radioactive source within said catheter assembly.

9. A catheter assembly for providing a radiation treatment in a target tissue of a patient, comprising:
a balloon arrangement including at least one balloon, said balloon arrangement for containing a radioactive fluid comprising a first radioactive source;
an inner catheter of a first diameter;
an outer catheter of a second diameter greater than the first diameter for receiving the inner catheter therein, at least one of said inner catheter and said outer catheter connected to said balloon arrangement;
a separate lumen located within said inner catheter; and
an additional radioactive source within said separate lumen.

10. A method of providing from a catheter assembly a radiation treatment in a target tissue of a patient, comprising the steps of: (a) positioning a balloon arrangement at a target site of the target tissue, the balloon arrangement having an outer balloon for containing a radioactive fluid and a coaxially disposed inner displacement balloon that is separately fillable with nonradiofluid fluidically distinct from the radioactive fluid; the inner balloon of a substantial diameter relative to a diameter of the outer balloon whereby upon inflation, the volume in which the radioactive fluid resides within a vicinity of the target tissue is reduced, thereby reducing the amount of radioactive gas required for treatment, and lumens for communicating the radioactive fluid and the nonradioactive fluid from respective supplies to the outer balloon and the inner balloon respectively, the inner balloon is fixed to a inner catheter of a first diameter and the outer balloon is fixed to an outer catheter of a second diameter greater than the first diameter for receiving the first catheter therein; (b) inflating the inner balloon with the nonradiofluid; (c) inflating the outer balloon with the radioactive fluid for a predetermined period effecting treatment at the target site; (d) defining upon inflation of both said inner balloon and said outer balloon a cylinder between said inner balloon and said outer balloon of radioactive fluid of limited thickness pressing against an interface of the target tissue at a said target site, while conforming well to said interface; and (e) controlling said thickness of said cylinder, further including the step of adding an additional radiation source to the catheter assembly.

* * * * *